(12) United States Patent
Ferguson

(10) Patent No.: US 7,713,933 B2
(45) Date of Patent: May 11, 2010

(54) PHARMACEUTICAL COMPOSITION CONTAINING AN ACTIVIN OR INHIBIN STIMULATOR

(75) Inventor: Mark W. J. Ferguson, High Peak (GB)

(73) Assignee: Renovo Limited, Manchester (GB)

( * ) Notice: Subject to any disclaimer, the term of this patent is extended or adjusted under 35 U.S.C. 154(b) by 641 days.

(21) Appl. No.: 10/654,994

(22) Filed: Sep. 5, 2003

(65) Prior Publication Data
US 2004/0052795 A1 Mar. 18, 2004

Related U.S. Application Data

(63) Continuation of application No. 09/043,110, filed as application No. PCT/GB96/02559 on Oct. 17, 1996, now abandoned.

(30) Foreign Application Priority Data
Oct. 21, 1995 (GB) ................................ 9521608.1

(51) Int. Cl.
*A61K 38/18* (2006.01)
*C07K 14/495* (2006.01)

(52) U.S. Cl. .......................................... 514/12; 53/350
(58) Field of Classification Search ........................ None
See application file for complete search history.

(56) References Cited

U.S. PATENT DOCUMENTS

| | | | |
|---|---|---|---|
| 5,071,834 A | | 12/1991 | Burton et al. |
| 5,102,868 A | | 4/1992 | Woodruff et al. |
| 5,145,680 A | * | 9/1992 | Hayashi ...................... 424/427 |
| 5,196,192 A | * | 3/1993 | De Kretser et al. ....... 424/158.1 |
| 5,216,004 A | | 6/1993 | Perrine |
| 5,387,576 A | | 2/1995 | Mitrani |
| 5,413,989 A | | 5/1995 | Ogawa et al. |
| 5,428,011 A | | 6/1995 | Sheth et al. |
| 5,753,612 A | | 5/1998 | Mitrani |
| 5,885,794 A | | 3/1999 | Mathews et al. |
| 5,888,720 A | | 3/1999 | Mitrani |

FOREIGN PATENT DOCUMENTS

| | | | |
|---|---|---|---|
| EP | 0 617 966 | | 10/1994 |
| GB | 2265310 A | * | 9/1993 |
| JP | A-6-506360 | | 7/1994 |
| JP | 7-149659 | | 6/1995 |
| JP | A-10-509592 | | 9/1998 |
| WO | WO 89/11862 | | 12/1989 |
| WO | WO 91/12334 | | 8/1991 |
| WO | WO 92/04913 | | 4/1992 |
| WO | WO 92/15323 | | 9/1992 |
| WO | WO 92/17206 | * | 10/1992 |
| WO | WO 93/19769 | | 10/1993 |
| WO | WO 95/26203 | | 10/1995 |
| WO | WO 96/15226 | | 5/1996 |

OTHER PUBLICATIONS

JP 7149659 Derwent WPI Abstract Accession No. 95-245599/32—English Abstract.
Guseinov, "Dynamics of healing of purulent wounds under the influence of immunoregulatory drugs", Arkh Patol 50(9):28-34 (1988)—English Abstract.
Border et al, "Transforming Growth Factor β in Tissue Fibrosis", The New England Journal of Medicine 331 (19):1286-1292 (1994).
Munz et al, "Overexpression of activin A in the skin of transgenic mice reveals new activities of activin in epidermal morphogenesis, dermal fibrosis and wound repair", The EMBO Journal 18(9):5205-5215 (1999).
Werner et al, "Roles of activin in tissue repair, fibrosis, and inflammatory disease", Cytokine & Growth Factor Reviews 17:157-171 (2006).
Andreev et al, "Expression of bone morphogenetic proteins (BMPs), their receptors, and activins in normal and scarred conjunctiva: Role of BMP-6 and activin-A in conjunctival scarring?", Experimental Eye Research 83: 1162-1170 (2006).
Sulyok et al, "Activin: an important regulator of wound repair, fibrosis, and neuroprotection", Molecular and Cellular Endocrinology 225:127-132 (2004).
Wankel et al, "Impaired wound healing in transgenic mice overexpressing the activin antagonist follistatin in the epidermis", The EMBO Journal 20(19):5361-5372 (2001).
Ferguson and O'Kane, Scar-free healing: from embryonic mechanisms to adult therapeutic intervention, *Phil. Trans. R. Soc. Lond*, B 359:839-850 (2004), Published online Apr. 20, 2004.
Occleston et al, "Prevention and reduction of scarring in the skin by Transforming Growth Factor beta 3 (TGF β3): from laboratory discovery to clinical pharmaceutical", J. Biomater. Sci. Polymer Edn. 19(8):1047-63 (2008)— Uncorrected Proof Copy.
Shah et al, "Neutralisation of TGF-$\beta_1$ and TGF-$\beta_2$ or exogenous addition of TGF-$\beta_3$ to cutaneous rat wounds reduces scarring", Journal of Cell Science 108:985-1002 (1995).
Renovo Phase II Clinical Trial RN1001-1011. RNS announcement, released to the London Stock Exchange Sep. 28, 2006, Renovo Announces Highly Positive Phase II Trial Results for Juvista.
Renovo Phase II Clinical Trial RN1001-0050, RNS announcement, released to the London Stock Exchange Sep. 12, 2007, Renovo Group PLC, "Statistically significant Efficacy of Juvista Demonstrated in Phase 2 Trial Using Drug Substance Manufactured by Lonza Biologics".
Cox, David A., "Transforming Growth Factor-Beta 3.", Cell Biology International 19(5):357-371 (1995).
Hirshberg et al, "TGF-[beta]3 in the Treatment of Pressure Ulcers: A Preliminary Report", Advances in Skin & Wound, Care 14(2):91-95 (2001).
LeGrand, Edmund K., "Preclinical Promise of Becaplermin (rhPDGF-BB) in Wound Healing", Am. J. Surg. 176(Suppl 2A):48S-54S (1998).

(Continued)

*Primary Examiner*—David S Romeo
(74) *Attorney, Agent, or Firm*—Nixon & Vanderhye P.C.

(57) ABSTRACT

The present invention concerns stimulators of Activin and/or Inhibin for use in promoting the healing of wounds and fibrotic disorders with reduced scarring, together with medicaments and methods for promoting the healing of wounds and fibrotic disorders with reduced scarring.

4 Claims, No Drawings

OTHER PUBLICATIONS

Weiman et al, "Efficacy and Safety of a Topical Gel Formulation of Recombinant Human Platelet-Derived Growth Factor-BB (Becaplemin) in Patients With Chronic Neuropathic Diabetic Ulcers", Diabetes Care 21(5):822-827 (1998).

Nanney, Lillian B., "Epidermal and Dermal Effects of Epidermal Growth Factor During Wound Repair", J. Invest. Dermatol. 94:624-629 (1990).

Brown et al, "Enhancement of Wound Healing By Topical Treatment With Epidermal Growth Factor", N. Engl. J. Med. 321:76-79 (1989).

Occleston et al, "Prevention and reduction of scarring in the skin by Transforming Growth Factor beta 3 (TGF β3): from laboratory discovery to clinical pharmaceutical", J. Biomater. Sci. Polymer Edn. 19(8):1047-1063 (2008).

* cited by examiner

PHARMACEUTICAL COMPOSITION CONTAINING AN ACTIVIN OR INHIBIN STIMULATOR

This application is a continuation of application Ser. No. 09/043,110, filed Sep. 21,1998, now abandoned, which is a 371 of PCT/GB96/02559, filed Oct. 17, 1996, the entire contents of which are hereby incorporated herein by reference.

The present invention concerns pharmaceutical preparations for promoting the healing of wounds or fibrotic disorders, in particular for promoting the healing of wounds or fibrotic disorders with reduced scarring, and for promoting the healing of chronic wounds.

By "wounds or fibrotic disorders" is meant any condition which may result in the formation of scar tissue. In particular, this includes the healing of skin wounds, the repair of tendon damage, the healing of crush injuries, the healing of eye wounds, including wounds to the cornea, the healing of central nervous system (CNS) injuries, conditions which result in the formation of scar tissue in the CNS, scar tissue formation resulting from strokes, and tissue adhesion, for example, as a result of injury or surgery (this may apply to e.g. tendon healing and abdominal strictures and adhesions). Examples of fibrotic disorders include pulmonary fibrosis, glomerulonephritis, cirrhosis of the liver, systemic sclerosis, scleroderma, proliferative vitreoretinopathy, repair following myocardial infarction, including myocardial hibernation.

In particular, there is a lack of compositions for promoting the healing of wounds or fibrotic disorders with reduced scarring. Scar tissue formation, although providing mechanical strength to a healed wound, can be unsightly and may impair the function of the tissue.

This is particularly the case in wounds which result in scar tissue formation in the CNS, the scar tissue inhibiting the reconnection of severed or re-growing nerve ends, so significantly affecting their function.

There is also a lack of compositions for use in the treatment of chronic wounds, for example venous ulcers, diabetic ulcers and bed sores (decubitus ulcers), especially in the elderly and wheel chair bound patients. Such compositions may be extremely useful in patients where wound healing is either slow or in whom the wound healing process has not yet started. Such compositions may be used to "kick-start" wound healing and may then be used in combination with compositions (e.g. those of PCT/GB93/00586) which promote the healing of wounds or fibrotic disorders with reduced scarring. Hence not only may a chronic wound be healed, but it may be healed with, reduced scarring.

According to the present invention there is provided a stimulator of Activin and/or Inhibin for use in promoting the healing of wounds and fibrotic disorders with reduced scarring.

By 'stimulator' is meant anything which may stimulate the quantity or efficacy of active Activin and/or active Inhibin at a site. This may be Activin or Inhibin itself (or a pharmaceutically acceptable salt thereof) or a fragment or a partially modified form thereof. Partial modification may for example be by way of addition, deletion or substitution of amino acid residues. A substitution may for example be a conserved substitution. Partially modified molecules may, for example, have a longer half-life than their parent molecule, or they may have a different binding affinity for their receptors. A fragment may comprise a least that part of Activin or Inhibin which is required to allow it to stimulate its receptors. Alternatively, a stimulator may, for example, be an inhibitor of Activin metabolism, or it may be a stimulator of Activin synthesis, or it may be a bioprecursor of activin or inhibin. For example, it may be an analogue of a fragment of activin or inhibin which is bound by a degradative enzyme, for example a mimotope. (Geysen, H. M. et al., 1987, Journal of Immunological Methods, 102: 259-274) made to a fragment of Activin or Inhibin which is bound by enzyme which degrades it. Such a mimotope can bind to the receptor site of the enzyme, competitively inhibiting the binding of Activin or Inhibin (as appropriate) to the enzyme and thereby inhibiting its degradation.

It may be an antagonist of an antagonist of Activin or Inhibin. For example, it may be an antagonist of Follistatin.

Activin is a member of the TGFβ superfamily, and like the other members of this family, activins are dimeric proteins, composed of disulphide linked beta A or beta B subunits. Three different forms of Activin have been identified in vivo: Activin A (beta a, beta a), Activin B (beta b, beta b) and Activin AB (beta a, beta b). Herein, by "Activin" is meant all possible forms of activin. Inhibins are heterodimers of beta a or beta b chains together with a common alpha chain and are called Inhibin A (alpha beta a) and Inhibin B (alpha beta b). Herein, by "Inhibin" is meant all possible forms of inhibin (Massague, J., 1990, "The Transforming Growth Factor Beta Family", Annual Review of Cellular Biochemistry, 6: 587-641. Vale, W. et al., 1990, "The Inhibin/Activin Family of Hormones and Growth Factors" in Peptide Growth Factors and Their Receptors, Volume II, M. B. Sporn and A. B. Roberts (eds), Springer-Verlag, pages 211-248).

The biological response to Activins or Inhibins is transduced by receptors which exist as heteromeric complexes of type 1 receptors (called Activin receptor like kinases (Alk) 2 and 4) and type 2 receptors which are transmembrane serine threonine kinases (Matthews, L. S. and Vale, W. W., 1993, "Molecular and Functional Characterisation of Activin Receptors", Receptor Volume 3, pages 173-181). Follistatin is an Activin binding protein which acts as an Activin antagonist in vitro, but in vivo may present Activins to their receptors (Michael, U. et al., 1993, "Follistatins more than follicle stimulating hormone suppressing proteins", Molecular and Cellular Endocrinology, Volume 91, pages 1-11).

Activin increases the number of gonadotrophs in the pituitary and causes differentiation of ovarian granulosa cells (May, K. E., 1994, "Inhibin and Activin: Molecular Aspects of Regulation and Function", TEM 5: 407-415). Activin A also enhances the differentiation or neuronal cells (Schubert, D. et al., 1990, "Activin is a nerve cell survival molecule", Nature, 344: 868-870), stimulates differentiation of megakaryocytes and erythroid cells (Nishimura, M. et al., 1991, "Effect of erythroid differentiation factor on megakaryocytic differentiation of L8057, a murine megakaryoblastic leukaemia cell line", Biochem Biophysics Research Communication, 181: 1042-1047) and induces mesoderm formation during early Xenopus development (Smith, J. C. et al., 1990, "Identification of a potent Xenopus mesoderm inducing factor as a homologue of Activin A", Nature, 345: 729-731).

Targeted disruption of the Activin beta A chain resulted in mice with craniofacial defects which died within 24 hours after birth (Matzuk, M. M. et al., 1995, "Functional analysis of activins during mammalian development", Nature, 274: 354-356). These mice also lacked whiskers and had abnormal whisker follicles. Activin beta A chain has been detected in the mesenchyme of developing hair follicles and embryonic skin, but not new born or adult skin (Roberts, V. J. et al., 1991, "Expression of Inhibin/Activin sub-unit messenger ribonucleic acids during rat embryogenesis", Endocrinology 128: 3122-3129; Roberts, V. J. and Barth, S. L., 1994, "Expression of messenger ribonucleic acids encoding the Inhibin/Activin system during mid and late gestation rat embryogenesis"; Endocrinology, 134: 914-923), in addition to the activin receptors Alk2 and Alk4 (Verschueren; K. et al., 1995, "Expression of type 1 and type 1B receptors for activin in mid-gestation mouse embryos suggests distinct functions in organogenesis", Mechanisms of Development, 52: 109-123). Disruption of the activin-binding protein, follistatin, in transgenic mice results in abnormal whisker development and hyperkeratotic skin. (Matzuk, M. M. et. al., 1995; "Multiple defects and perinatal death in mice deficient in follistatin", Nature, 374, 360-363). Disruption of the gene for the Activin/Inhibin beta b subunit resulted in subtle defects to eyelid development (Vassaiil, A. et al., 1994, "Activin/Inhibin beta b subunit chain disruption leads to defects in eyelid development and female reproduction", Genes and Development, 8: 414-427), whilst targeted disruption of the Inhibin alpha chain caused tumour formation in the gonads (Matzuk, M. M. et al., 1992, "Inhibin is a tumour suppressor gene with gonadal specificity in mice", Nature, 360: 313-319).

There have been no reports of the role of either Activin, Inhibin or follistatin during wound healing, scarring or fibrosis.

However, the present inventor has found that Activin and Inhibin in fact play roles in wound healing as non-fibrotic growth factors. High levels of expression of Activin and of Activin and Inhibin receptors have been found post-wounding at wound sites, similar to TGF-$\beta_3$ (see PCT/GB93/00586). Ibis observation is particularly surprising in light of the prior belief that. Activin and Inhibin are predominantly reproductive/erythroid/neurological/mesoderm inducing factors.

Activin and Inhibin have been found to be structurally similar to TGF-$\beta_3$, the similarity being greater than that with TGF-$\beta_1$ and TGF-$\beta_2$. It appears that Activin and Inhibin may in fact bind to receptors similar to those bound by TGF-$\beta_3$ and as such mediate the control of scarring via that route.

It has also been found that the Act 2a receptor, which is bound by Activin and which is believed to be bound by TGF-$\beta_3$, is upregulated in wound healing, especially on day 7 post-wounding. Table 1 details further the binding of the isoforms of the TGF-$\beta$ receptor family.

Hence Activin and Inhibin have similar anti-scarring properties to those of TGF-$\beta_3$ and as such Activin and Inhibin, may be used to similar effect (see, for example, PCT/GB93/00586).

The stimulator may be used in conjunction with a pharmaceutically acceptable carrier, diluent or excipient. It may be used in conjunction with a pharmaceutically acceptable carrier, diluent or excipient in the preparation of a medicament for promoting the healing of wounds and fibrotic disorders with reduced scarring. Accordingly, the present invention also provides the use of a stimulator of activin and/or inhibin in the preparation of a medicament for use in promoting the healing of wounds and fibrotic disorders with reduced scarring.

Two or more stimulators according to the present invention may of course be included in a single composition or medicament or used in a single treatment.

Pharmaceutically acceptable carriers, diluents and excipients are well known—see for example Remington's Pharmaceutical Sciences and US Pharmacopeia (1984) Mack Publishing Company, Easton, Pa.

Pharmaceutically acceptable carriers may for example comprise a neutral, sterile cream, gel or powder for topical application, or a sterile solution for injection, irrigation or inhalation or an aerosol, or may comprise a sterile dressing for topically covering a wound or may be in the form of a tablet or capsule for enteral administration, or the carrier may comprise a biopolymer patch or a slow release device for implantation.

Stimulators of activin and/or inhibin and medicaments manufactured or prepared according to the present invention may be in the form of a composition for topical administration as a cream, gel, powder or dressing; in a solution for injection, irrigation or inhalation or aerosol, or in the form of a tablet or capsule for enteral administration. They may also comprise a biodegradable polymer forming a patch, or an implantable control release device, useful in surgical operations having a large initial release followed by a slower release later. It will be appreciated that this list is not exhaustive, many other types of compositions being possible, such as might readily occur to one skilled in the art.

Other forms of the present invention in which are included a stimulator of activin and/or inhibin also include bandages; biocompatible, biodegradable, non-inflammatory delivery vehicles such as hyaluronic acid; implants; intradermal injections; systemic therapy for e.g. fibrosis or severe trauma or burns, for example by intraperitoneal, intravenous or oral administration; eye drops for corneal wounds or scarring; films and barriers for treating adhesions.

Application for compositions and agents for promoting the healing of wounds and fibrotic disorders with reduced scarring are well known (see for example PCT/GB93/00586, PCT/GB92/00570 and U.S. Pat. No. 5,520,926) and the present invention incorporates them accordingly.

The stimulator may be used in conjunction with a composition for promoting the healing of wounds or fibrotic disorders with reduced scarring.

The stimulator may be used in conjunction with a composition for promoting the healing of chronic wounds.

Also provided according to the present invention is a method for promoting the healing of wounds or fibrotic disorders with reduced scarring comprising stimulating Activin and/or Inhibin.

The stimulation may be achieved by administering to a site activin and/or inhibin itself or a stimulator of Activin and/or. Inhibin. By 'site' is meant a site of wounding or fibrotic disorder. The stimulator may be a stimulator according to the present invention. It may, for example, the an antagonist of Follistatin.

Activin and/or Inhibin may be stimulated immediately prior to wounding. It may be preferably stimulated immediately after wounding. It may be stimulated within 14 days of wounding, preferably within 7 days of wounding, more preferably within 3 days of wounding.

The method may be for use in conjunction with a method for promoting the healing of wounds or fibrotic disorders with reduced scarring.

The method may be for use in conjunction with a method for promoting the healing of chronic wounds.

The invention will be further apparent from the following description which show, by way of example only, forms of promotion of the healing of wounds and fibrotic disorders with reduced scarring.

EXPERIMENTAL

Initial studies were undertaken to determine the expression profile of Activin in wounded tissue, relative to control tissue. These resulted in the conclusion that exogenous addition of Activin, or its related molecule Inhibin (which binds to similar receptors to Activin) or antagonism of the binding protein of Activin (Follistatin) could have anti-scarring activity. This was then tested in two sets of experiments, the first involving the use of Activin A and the second using Inhibin. The conclusions of the experiments were that Activin and Inhibin have an anti-scarring effect.

Experiment 1

Wounding

Adult male CD1 mice were anaesthetized using halothane nitrous oxide and oxygen. Four wounds were placed on each animal, approximately one centimetre from the mid line, 20 and 40 centimetres from the base of the skull respectively. The wounds were 1 centimetre in length down to and through the panniculus carnosus. Animals were killed and wounds recovered on days 1, 3, 7, 14, 28, 60 and 80, post wounding. At least 4 wounds from 4 separate animals were analysed for each experiment. Wounds were excised, fixed in paraformaldehyde, dehydrated and embedded in wax in preparation for in situ hybridisation (under RNAase free conditions), or frozen in OCT (Miles Scientific), cryosectioned and utilized for immunocytochemistry.

For in situ hybridisation, antisense riboprobes were constructed against the Act 2a receptor, Act R1 (Alk 2) and Act RIB (Alk 4).

For immunocytochemistry, a primary antibody recognising Activin was used and detected using streptavadin biotin amplification using an FITC (fluorescein isothiocyanate) labelled secondary antibody.

As controls, non wounded adult and fetal E16 (embryonic day 16) skin were used.

Results

On days 3 and 7 post wounding, enhanced staining for Activin was detected in the wound site, predominantly in fibroblasts of the wound margin and granulation tissue. Staining had returned to near normal levels by 14 days post wounding. As the antibody predominantly recognises the Activin beta A chain, it is assumed that this is the predominant isoform in the granulation tissue.

The messenger RNA for the Act 2a receptor was up-regulated in the wound margin and granulation tissue on seven days post wounding. The Alk 2 (Act R1) receptor was expressed in the mesenchyme of normal skin, but no significant elevation was detected in the wound edge or granulation tissue. By contrast, Act RIB (Alk 4) receptor was present at a much lower level in the normal skin dermis but was up-regulated in the dermal wound margin and granulation tissue of the wounds, particularly on days 7 and 14, post wounding.

In normal adult mouse skin, Alk 2 and Alk4 were expressed predominantly in the dermis and epidermis, respectively. Staining for Activin in the normal adult skin was at a marked low level in the dermis. However, fetal skin from embryonic day 16 mice showed marked staining for activin, particularly in the fetal dermis.

These staining patterns suggest that Activin and its receptors are present in fetal skin and reinduced during wound healing in adult skin. As fetal wounds heal without scarring at embryonic day 16 (Whitby, D. J. and Ferguson, M. W. J., "The extracellular matrix of lip wounds in fetal, neonatal and adult mice", Development, 112: 651-668,1991) and with reduced levels of inflammation, and hence TGFβ1 and TGFβ2, but enhanced endogenous dermal levels of TGFβ3 (Whitby, D. J. and Ferguson, M. W. J., 1991, "Immunohistochemical localisation of growth factors and fetal wound healing", Developmental Biology, 147: 207-215), it might reasonably be assumed that Activin plays a role in this scarless fetal wound healing. Hence, exogenous addition of Activin, or its related molecule Inhibin (which binds to similar receptors to Activin) or antagonism of the binding protein of Activin (Follistatin) could have anti-scarring activity.

In order to test this, the following experiment was undertaken:

Experiment 2

Materials and Methods

Recombinant bovine Activin A (4 μg) was obtained from Innogenetics, Belgium (Cat. No. CY-035). Activin A was prepared by initially reconstituting the lyophilised powder in sterile phosphate buffered saline (PBS) containing 0.1% bovine serum albumin (BSA) and then diluting with PBS/BSA to give three doses: 100 ng/ml; 50 ng/ml; and 25 ng/ml.

Twelve adult male Sprague-Dawley rates, age- and weight-matched (220 g-250 g), were anaesthetised using a mixture of equal parts halothane, nitrous oxide and oxygen. The dorsal surfaces were shaved and swabbed with 70% alcohol. Four 1 cm linear full thickness (down to and including the panniculus carnosus) incisions were made at defined anatomical positions 5 cm and 8 cm from the base of the skull, and 1 cm each side of the midline.

Of the four wounds per animal, two were treated with a 100 μl dose of Activin A, one with 100 μl of PBS, and the other remained unmanipulated. All injections were intradermal, approximately 50 μl delivered down each side of the incision as close as possible to the wound without rupturing it, and were administered once daily for three days, starting immediately prior to wounding (Day 0).

The twelve animals were divided into three groups according to the dose administered. Four animals received daily 100 μl injections of 100 ng/ml Activin A (i.e. 10 ng/100 μl injection), four received 50 ng/ml (i.e. 5 ng/100 μl injection) and the remaining four were treated with 25 ng/ml (i.e. 2.5 ng/100 μl injection). The wounds were uncovered and unsutured. Six animals, two from each treatment group, were killed 7 days pw (post-wounding) and the remaining six killed at 80 days post-wounding, all by chloroform overdose followed by dislocation of the neck. A PC based image capture system was used to save macroscopic images of the intact, shaved skin. The dorsal skin was removed and the fill thickness wounds excised with a margin of approximately 0.5 cm of normal skin around the wound. One half of the tissue was fixed in formal saline and processed for routine wax histology and the other half immersed in OCT embedding medium and snap frozen over liquid nitrogen for immunocytochemical analysis.

Wax Histology

7 μm sections were cut on a standard microtome and the sections stained with Haematoxylin & Eosin to examine cellularity and angiogenesis, and Masson's Trichrome stain for collagen organisation.

Results

Macroscopic

A visual analogue scoring system was devised which ranged from 0 representing normal, unwounded skin, to 10 representing hypertrophic scarring. A 10 cm unmarked line was drawn on a blank piece of paper and the four scars on the dorsal surface of each freshly killed rat were scored by placing a mark along the line between 0 and 10, with a separate line for each scar. Only the 80 day scars were scored (i.e. 6 rats).

The macroscopic appearances of the wounds treated with Activin A were very good. The scars were quite variable but the lowest doses produced the best quality macroscopic scars when compared to the controls.

Microscopic 10 ng/100 μl Injection:

At 7 days pw, the wounds were re-epithelialised and the epithelium had flattened out, similar to unwounded epithelium. One consistent observation at 7 days post-wounding (pw) was that there were not many inflammatory cells at the top of the wound, but quite a lot at the base. The control wounds (unmanipulated and PBS treated) were also re-epithelialised but had more inflammatory cells distributed throughout the wound.

At 80 days pw, the microscopic appearance of the scars was very good. Another visual analogue scoring system was used, ranging from 0 representing normal skin to 10 representing hypertrophic scaring. The average scores are shown in Table 2. The average score for treated wounds was 2.65, PBS treated 3.3, and unmanipulated 3.65. The orientation of collagen in the treated wounds was more like that of normal skin, the collagen bundles being less densely packed, larger, and having a more basket-weave appearance (unwounded dermis has collagen bundles arranged in a basket-weave architecture), particularly towards the epidermis.

5 ng/100 μl Injection:

At 7 days pw, the wounds were all re-epithelialised and quite cellular throughout and treated wounds appeared similar to control wounds. There was some variation in the treated wounds, with some being very cellular, and others not containing as many inflammatory cells.

At 80 days pw, the dermal architecture was good, averaging a score of 3.13, compared to PBS and unmanipulated control wounds which averaged 5.5 and 4.1 respectively. The collagen was more open and there were thicker bundles, again particularly at the top of the wound site near the epidermis.

2.5 ng/100 μl Injection:

At 7 days pw, the treated wounds resembled the control wounds.

At 80 days pw, the treated wounds had a reasonable collagen architecture, and averaged a score of 5.25, compared to PBS and unmanipulated control wounds which averaged 5.45 and 4.25 respectively.

Conclusions

These experiments show that the TGF-β family member Activin A has an anti-scarring effect.

Both 5 ng/100 μl injection and 10 ng/100 μl injection treatment regimes showed considerable improvement in scarring relative to control wounds. The 2.5 ng/100 μl injection treatment regime was probably too low. It is interesting that the highest dose appears to reduce the influx of inflammatory cells into the wound an effect similar to that achieved with TGF-$β_3$. The microscopic appearance of wounds at 80 days pw which had been treated with 10 ng/100 μl injection Activin A was better than the controls, and 5 ng/100 μl injection was also better than controls. Comparison between 10 ng/100 μl injection and 5 ng/100 μl injection treatments showed that the 10 ng/100 μl injection treatment was superior but that the control wounds in these animals were also better, possibly the result of systemic effects of the high dose of Activin A. The lowest dose (2.5 ng/100 μl) also slightly improved scaring although the microscopic results were closer to the control wounds.

The macroscopic appearance of the wounds was quite variable although the wounds treated with the middle (5 ng/100 μl injection) and lowest (2.5 ng/100 μl injection) doses appeared to be better than their respective controls. The wounds treated with the highest (10 ng/100 μl injection) dose were macroscopically quite variable, but an obvious effect may have been negated by the quality of the control wounds which were on the same animal and therefore perhaps improved by systemic effects of the high dose of Activin A.

Experiment 3

Materials and Methods

Porcine Inhibin (20 μg per vial) was obtained from the National Institute for Biological Standards and Control, Potters Bar, UK (Cat No 86/690)

The inhibin was reconstituted in sterile PBS with 0.1% BSA to a stock solution of 20 μg/ml and further diluted to 0.1, 1 and 5 μg/ml (i.e. 10, 100 and 500 ng/100 μl injection).

Pilot Experiment

Twelve adult male Sprague-Dawley rats, age- and weight-matched (220 g-250 g), were anaesthetised using a mixture of equal parts halothane, nitrous oxide and oxygen. The dorsal surfaces were shaved and swabbed with 70% alcohol. Four 1 cm linear full thickness (down to and including the panniculus carnosus) incisions were made at defined anatomical positions: 5 cm and 8 cm from the base of the skull, and 1 cm each side of the midline.

Two wounds per animal were treated with a 100 μl dose of Inhibin, one with 100 μl of either PBS/BSA or PBS alone, and one remained unmanipulated. All injections were intradermal. The first injection was administered at the wound site immediately prior to wounding (day 0) and then for two days following wounding. 50 μl was delivered down each side of the incision as close as possible to the wound without rupturing it.

The 12 animals were divided into three groups according to the dose administered. Four animals received daily injections of 10 ng/100 μl, four received 100 ng/100 μl and the remaining four were treated with 500 ng/100 μl. The wound were uncovered and unsutured. Six animals, two from each treatment group, were killed 7 days post wounding and the remaining six killed at 80 days post-wounding, all by chloroform overdose followed by dislocation of the neck. A PC based image capture system was used to save macroscopic images of the intact, shaved skin. The dorsal skin was removed and the full thickness wounds excised with a margin of approximately 0.5 cm of normal skin around the wound. One half of the tissue was fixed in formal saline and processed for routine wax histology and the other half immersed in OCT embedding medium and snap frozen over liquid nitrogen for immunocytochemical analysis.

Wax Histology: 7 μm sections were cut on a standard microtome and the sections stained with Haematoxylin & Eosin to examine cellularity and angiogenesis, and Masson's Trichorome stain for collagen organisation.

Results

Macroscopic

A visual analogue scoring system was devised which ranged from 0 representing normal, unwounded skin, to 10 representing hypertrophic scarring. A 10 cm unmarked line was drawn on a blank piece of paper and the four scars on the dorsal surface of each freshly killed rat were scored by placing a mark along the line between 0 and 10, with a separate line for each scar. Only the 80 day scars were scored (i.e. 6 rats, 24 wounds).

The appearances of the wounds treated with Inhibin were variable at 80 days. Of the wounds treated with the highest dose (500 ng/injection), one was an extremely good, fine linear scar and the others were similar to controls. Wounds treated with PBS/BSA were also similar to unmanipulated controls. The wounds treated with the middle dose of Inhibin were also quite similar to control wounds. Two of the wounds treated with the lowest dose had very fine linear scars, barely discernible from the surrounding unwounded dermis, while the other scars were similar in appearance to controls. Overall, the macroscopic results: suggested that the lowest into highest doses of Inhibin may, improve scarring.

Histology

7 Days Post-Wounding

Overall, the treated wounds resembled unmanipulated or PBS treated control wounds at 7 days. The wounds contained a lot of inflammatory cells, had re-epithelialised and were variable in width. The control wounds treated with PBS/BSA were very cellular, were very wide and in one case had not re-epithelialised.

80 Days Post-Wounding

A visual analogue scoring system also ranging from 0 representing normal, unwounded skin, to 10 representing hypertrophic scarring, was used to score the histology slides at 80 days post-wounding (Table 3). Some of the wounds treated with the highest dose of Inhibin (500 ng/100 μl injection) had a good dermal architecture, the collagen bundles were thick and in a random organisation resembling the normal basket-weave pattern of unwounded dermis. In most of the other wounds the collagen was dense and in parallel alignment, resembling the control wounds. The average score was 4.49 for wounds treated with 500 ng Inhibin/100 μl injection, 5.6 for untreated control wounds and 5.08 for PBS control wounds. Wounds treated with the middle dose (100 ng/100 μl injection) were similar to PBS controls (scores were 7.58 and 7.9 respectively), the collagen fibres were thick but densely packed, mostly at the top of the wound. (The unmanipulated controls had a good score of 4.9 in this group).

The collagen in the wounds treated with the lowest dose of Inhibin (10 ng/100 μl injection) was orientated in an open, random fashion but once again at the top of the wound, the collagen was quite densely packed. These wounds scored similarly to the controls (see Table 3).

Conclusions

The highest dose of Inhibin appeared to have a slight anti-scarring effect, with the microscopic results correlating with macroscopic data. The PBS/BSA control appeared to produce worse scars at 80 days post-wounding and at 7 days post-wounding the wounds contained much larger numbers of inflammatory cells. Reconstituting the Inhibin in PBS alone may have a more marked anti-scarring effect.

Experiment 4

Follow-up Experiment
Materials and Methods

Porcine Inhibin (20 μg per vial) was obtained from the National Institute for Biological Standards and Control, Potters Bar, UK (Cat. No. 86/690).

The Inhibin was reconstituted in sterile PBS with 0.1% BSA to a stock solution of 20 μg/ml and further diluted to 2.5, 10 and 15 μg/ml (i.e. 250, 1000 and 1500 ng/100 μl injection).

The surgical technique used was as before except for the numbers of animals used (18; n=72) and there was an extra time point at 40 days post-wounding.

Two wounds per animal were treated with a 100 μl dose of Inhibin, one with 100 μl of either PBS/BSA or PBS alone, and one remained unmanipulated. All injections were intradermal. The fist injection was administered at the wound site immediately prior to wounding (day 0) and then for two days following wounding. 50 μl was delivered down each side of the incision as close as possible to the wound without rupturing it.

The 18 animals were divided into three groups according to the dose administered. Six animals received daily 100 μl injections of 250 ng, six received 1000 ng and the remaining six were treated with 1500 ng. The wounds were uncovered and unsutured. Six animals, two from each treatment group were killed 7 days post-wounding six at 40 days post-wounding and the remaining six killed at 80 days post-wounding, all by chloroform overdose followed by dislocation of the neck. A PC based image capture system was used to save macroscopic images of the intact, shaved skin. The dorsal skin was removed and the fill thickness wounds excised with a margin of approximately 0.5 cm of normal skin around the wound. One half of the tissue was fixed in formal saline and processed for routine wax histology and the other half immersed in OCT embedding medium and snap frozen over liquid nitrogen for immunocytochemical analysis.

Wax Histology

7 μm sections were cut on a standard microtome and the sections stained with Haematoxylin & Eosin to examine cellularity and angiogenesis, and Masson's Trichrome stain for collagen organisation.

Results

Macroscopic

The standard visual analogue scoring system was used which ranged from 0 representing normal unwounded skin, to 10 representing hypertrophic scarring. A 10 cm unmarked line was drawn on a blank piece of paper and the four scars on the shaved dorsal surface of each freshly killed rat were scored by placing a mark along the line between 0 and 10, with a separate line for each scar. Only the 40 and 80 day scars were scored (i.e. 6 rats, 24 wounds at each time point).

Macroscopic analysis at 40 days suggested that the wounds treated with the highest dose of inhibin (1500 ng/100 μl injection had the least obvious scars (average score 4.1) compared to wounds which had been treated with 1000 ng/100 μl injection or 250 ng/100 μl injection (average scores of 5 and 4.6 respectively). However, at 80 days, the average macroscopic score (4.51) for the wounds treated with the lowest dose of inhibin (250 ng/100 μl injection) was considerably better than scores for the two higher doses (1500 ng/100 μl injection and 1000 ng/100 μl injection), which had similar average scores of 5.275 and 5.375 respectively.

Histology
7 Days Post-Wounding

All wounds had re-epithelialised at 7 days post-wounding. There were no differences between PBS treated and unmanipulated control wounds. There were high numbers of inflammatory cells at the base of the wounds treated with 1500 ng/100 μl injection and 1000 ng/100 μl injection and there was not a large amount of new collagen compared to control wounds. The wounds treated with 250 ng/100 μl injection were narrow did not contain many inflammatory cells and had a lot of new collagen.

40 and 80 Days Post-Wounding

The standard visual analogue scoring system was used to evaluate the 40 and 80 day wounds. The results are shown in Table 4.

At 40 days, the wounds treated with 250 ng/100 μl inhibin injections had the worst dermal architecture, the collagen was densely packed and in parallel alignment, reflected in an average score of 7.4. The wounds treated with 1000 ng/100 μl injection had an average score of 6.0 and were similar to PBS treated control wounds (6.2). The unmanipulated control wounds in the groups treated with 1000 and 1500 ng/100 μl injection had the best average scores, possibly indicating a systemic effect. The histological scores for the wounds treated with 1500 ng/100 μl injection were in agreement with the scores for macroscopic appearance, and reflected the superior dermal architecture observed at this stage (4.7).

At 80 days post-wounding, the histological appearance of the wounds treated with 250 ng/100 μl injection was better than the wounds treated with 1000 or 1500 ng/100 μl injection. The collagen bundles were less densely packed and in a more random organisation, particularly at the top of the scar, just below the epidermis. Only one scar treated with this dose was wide, and of poor quality. The wounds which had received 1000 ng/100 μl injection treatment had densely packed collagen throughout the wounds and the wounds treated with 1500 ng/100 μl injection, although one had relatively open collagen orientation at the top, were in general very wide at the base where the collagen was particularly dense.

SUMMARY

These results suggest that the lowest dose of inhibin used in this investigation. (250 ng/100 μl injection) had anti-scarring effects. The pilot experiment suggested that a dose of 500 ng/100 μl injection also had slight anti-scarring effects. It appears therefore that exogenous addition of inhibin has an antiscarring effect and the data suggest the optimum dose of inhibin is between 250 and 500 ng/100 μl injection in this treatment regime.

TABLE 1

The TGF-β Receptor family and their known affinities for TGF-$\beta_{1, 2, and 3}$, Activin, BMP 2,4 and MIS

| | TGF-β | Activin | BMP 2,4 | MIS |
|---|---|---|---|---|
| Type I Receptors | | | | |
| TGF-β RI | ✓ | | | |
| Act R-Iβ | | ✓ | | |
| Atr-I | | ✓ | | |
| BRK-I | | | ✓ | |
| RPK-I | | | ✓ | |

TABLE 1-continued

The TGF-β Receptor family and their known affinities for TGF-$β_{1, 2, and 3}$, Activin, BMP 2,4 and MIS

|  | TGF-β | Activin | BMP 2,4 | MIS |
|---|---|---|---|---|
| Act R-I |  | ✓ |  |  |
| TSR-I | ✓ | ✓ |  |  |
| Brk-43E |  |  | ✓ |  |
| Brk-25D |  |  | ✓ |  |
| DAF-I |  |  |  |  |
| Type II Receptors |  |  |  |  |
| Act R-II |  | ✓ |  |  |
| Act R-IIB |  | ✓ |  |  |
| Atr II |  | ✓ |  |  |
| TGF-β RII | ✓ |  |  |  |
| Daf4 |  |  | ✓ |  |
| C14 |  |  |  | ? |

BMP2,4 = Bone Morphogenetic Proteins
MIS = Mullerian Inhibiting Substance

TABLE 2

Average Histological Scores (80 days post-wounding) Rat Wounds Treated with Activin A

| Group | Dose (ng/100 µl injection) | Average Score |  |  |
|---|---|---|---|---|
|  |  | Treated Wounds | PBS | U |
| A | 10 | 2.625 | 3.3 | 3.65 |
| B | 5 | 3.13 | 5.5 | 4.075 |
| C | 2.5 | 5.25 | 5.45 | 4.25 |

Dosages relate solely to Activin A treated wounds
PBS = PBS treated control wounds
U = Unmanipulated control wound

TABLE 3

Average Histological Scores (80 days post-wounding) of Rat Wounds Treated with Inhibin.

| Group | Dose (ng/100 µl injection) | Average Score |  |  |  |
|---|---|---|---|---|---|
|  |  | Treated Wounds | PBS | PBS/BSA | U |
| A | 10 | 5.13 | 4.75 | 5.7 | 4.675 |
| B | 100 | 7.58 | 7.9 | 8.0 | 4.9 |
| C | 500 | 4.49 | 5.08 |  | 5.6 |

Dosages relate solely to Activin A treated wounds
PBS = PBS treated control wounds
PBS/BSA = PBS/BSA treated control wounds
U = Unmanipulated control wound

TABLE 4

Average Histological Scores (40 days and 80 days post-wounding) of Wounds Treated with Inhibin

|  | Average Score | |
|---|---|---|
|  | 40 days | 80 days |
| Group A: Dose |  |  |
| 250 ng/100 µl injection | 7.4 | 4.51 |
| PBS | * | 5.15 |
| U | 7.6 | 5.25 |
| Group B: Dose |  |  |
| 1000 ng/100 µl injection | 6.0 | 5.225 |
| PBS | 6.2 | — |
| U | 3.9 | — |
| Group C: Dose |  |  |
| 1500 ng/100 µl injection | 4.7 | 5.2 |
| PBS | 4.6 | — |
| U | 2.0 | — |

*this denotes where results are not yet available.

The invention claimed is:

1. A method for promoting the healing of an incisional dermal wound with reduced macroscopic scarring in a subject in need thereof, said method comprising intradermally administering up to about 5 ng of Activin per centimeter of said incisional dermal wound so that said healing with reduced macroscopic scarring is promoted.

2. The method according to claim 1 wherein Activin is administered in conjunction with a pharmaceutilcally acceptable carrier, diluent or excipient.

3. The method according to claim 1 wherein Activin is used in conjunction with a further agent that promotes the reduction of scarring.

4. The method according to claim 1 wherein the amount of Activin administered is sufficient to bind receptors bound by TGF-$β_3$.

* * * * *